US011365243B2

(12) United States Patent
Diamond et al.

(10) Patent No.: US 11,365,243 B2
(45) Date of Patent: Jun. 21, 2022

(54) INHIBITION OF AUTISM SPECTRUM DISORDER USING DECOY ANTIGENS TO MATERNAL BRAIN-REACTIVE ANTIBODIES

(71) Applicant: The Feinstein Institutes for Medical Research, Manhasset, NY (US)

(72) Inventors: Betty A. Diamond, Bronx, NY (US); Simone Mader, Woodside, NY (US); Lior Brimberg, Bayside, NY (US); Peter Gregersen, Larchmont, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 143 days.

(21) Appl. No.: 16/852,755

(22) Filed: Apr. 20, 2020

(65) Prior Publication Data
US 2020/0247880 A1  Aug. 6, 2020

Related U.S. Application Data

(62) Division of application No. 15/760,660, filed as application No. PCT/US2016/054651 on Sep. 30, 2016, now Pat. No. 10,645,919.

(60) Provisional application No. 62/237,150, filed on Oct. 5, 2015.

(51) Int. Cl.
| | | |
|---|---|---|
| *C07K 16/18* | (2006.01) | |
| *A61K 38/17* | (2006.01) | |
| *A61P 25/28* | (2006.01) | |
| *G01N 33/68* | (2006.01) | |

(52) U.S. Cl.
CPC .............. *C07K 16/18* (2013.01); *A61K 38/17* (2013.01); *A61K 38/177* (2013.01); *A61K 38/1709* (2013.01); *A61K 38/1774* (2013.01); *A61P 25/28* (2018.01); *G01N 33/6896* (2013.01); *G01N 33/6893* (2013.01); *G01N 2800/28* (2013.01); *G01N 2800/38* (2013.01); *G01N 2800/50* (2013.01)

(58) Field of Classification Search
CPC .... C07K 16/18; A61K 38/17; G01N 2800/38; G01N 2800/50
See application file for complete search history.

(56) References Cited

U.S. PATENT DOCUMENTS

| | | |
|---|---|---|
| 2013/0137585 A1 | 5/2013 | Carayol et al. |
| 2013/0210037 A1 | 8/2013 | Van de Water et al. |

FOREIGN PATENT DOCUMENTS

| | | |
|---|---|---|
| JP | 2013501942 A | 1/2013 |
| WO | 2011019929 A1 | 2/2011 |
| WO | 2012149472 A2 | 11/2012 |
| WO | 2014124396 A1 | 8/2014 |

OTHER PUBLICATIONS

PCT International Search Report and Written Opinion dated Feb. 17, 2017 for PCT International Patent Application No. PCT/US2016/054651, 13 pages.
Communication Supplementary European Search Report dated Mar. 21, 2019 in connection with European Patent Application No. 16854111.8.
Peagarikano et al., "Absence of CNTNAP2 Leads to Epilepsy, Neuronal Migration Abnormalities, and Core Autism-Related Deficits," Cell, vol. 147, No. 1, Aug. 26, 2011, pp. 235-246.
Brimberg et al., "Caspr2-Reactive Antibody Cloned from a Mother of an ASD Child Mediates an ASD-Like Phenotype in Mice," Molecular Psychiatry, vol. 21, No. 12, Oct. 4, 2016, pp. 1663-1671.
Poot, "Connecting the CNTNAP2 Networks With Neurodevelopmental Disorders," Molecular Syndromology, vol. 6, Feb. 3, 2015, pp. 7-22.
Falivelli et al., "Inherited Genetic Variants in Autism-Related CNTNAP2 Show Perturbed Trafficking and ATF6 Activation," Human Molecular Genetics, vol. 21, No. 21, Aug. 7, 2012, pp. 4761-4773.
Tanabe et al., "CASPR2 Forms a Complex With GPR37 Via MUPP1 But Not With GPR37(R558Q), an Autism Spectrum Disorder-Related Mutation," Journal of Neurochemistry, vol. 134, 2015, pp. 783-793.
Japanese Office Action dated Oct. 6, 2020 from Japanese Patent Appln. No. 2018-517133 (with English language translation attached).
Coutinho et al., "Maternal-to-Foetal Transfer of CASPR2 Antibodies Associated With Autistic Features in Adult Mouse Offspring," Annals of Neurology, vol. 78, Supp. 19, Section M132WIP, Sep. 25, 2015, pp. S81-S82.

*Primary Examiner* — Olga N Chernyshev
(74) *Attorney, Agent, or Firm* — Amster, Rothstein & Ebenstein LLP

(57) ABSTRACT

Methods of diagnosis and methods of treatment and prevention for autism spectrum disorder are provided using decoy antigens to maternal brain-reactive antibodies.

10 Claims, 6 Drawing Sheets

INHIBITION OF AUTISM SPECTRUM DISORDER USING DECOY ANTIGENS TO MATERNAL BRAIN-REACTIVE ANTIBODIES

CROSS-REFERENCE TO RELATED APPLICATIONS

This application is a divisional of U.S. patent application Ser. No. 15/760,660, filed Mar. 16, 2018, which is a U.S. national stage of PCT International Patent Application No. PCT/US2016/054651, filed Sep. 30, 2016, which claims the benefit of U.S. Provisional Application No. 62/237,150, filed Oct. 5, 2015, the contents of each of which are hereby incorporated by reference in their entirety.

STATEMENT OF GOVERNMENT SUPPORT

This invention was made with government support under grant number W81XWH-14-1-0369 awarded by the Department of Defense and grant number MH106195 awarded by the National Institutes of Health. The government has certain rights in the invention.

BACKGROUND OF THE INVENTION

Throughout this application various patents and other publications are referred to by number in parenthesis. Full citations for the references may be found at the end of the specification. The disclosures of these references and all patents, patent application publications and books referred to herein are hereby incorporated by reference in their entirety into the subject application to more fully describe the art to which the subject invention pertains.

Autism spectrum disorder (ASD) is a group of neurodevelopmental syndromes characterized by communication and social interaction difficulties as well as stereotypic behaviors. In 2013, the Center for Disease Control estimated that 1 in 88 American children have ASD and the diagnosis has increased 10-fold over the past four decades. While there is no cure for ASD, early detection and intervention can significantly improve the cognitive ability and language skills of those afflicted.

The present invention address the need for diagnosis and inhibitory treatments for autism spectrum disorder using decoy antigens to maternal brain-reactive antibodies.

SUMMARY OF THE INVENTION

A method is provided for inhibiting or reducing development of an autism spectrum disorder in a fetus or an infant comprising administering to a mother pregnant with the fetus or prior to the fetus being born as an infant while the mother is pregnant, an amount of an agent which binds an antibody directed to Caspr2, KCNAB2, KCNAB1, endothelial integrin ligand (EDIL3), IVD, brain specific sultatransferase (SULT4A1), TNIP2, retinoic acid induced 16 (RAI16) or GDP D5, effective to inhibit or reduce development of an autism spectrum disorder in a fetus or an infant.

A method is also provided for inhibiting or reducing development of an autism spectrum disorder in a fetus or an infant comprising extracorporeally contacting blood of a mother pregnant with the fetus or prior to the fetus being born as an infant while the mother is pregnant, with an amount of an agent which binds an antibody directed to Caspr2, KCNAB2, KCNAB1, endothelial integrin ligand (EDIL3), IVD, brain specific sultatransferase (SULT4A1), TNIP2, retinoic acid induced 16 (RAI16) or GDP D5 so as to reduce the blood levels of an antibody directed to Caspr2, KCNAB2, KCNAB1, EDIL3, IVD, SULT4A1, TNIP2, RAI16 or GDP D5, and recirculating the blood so treated back into the mother effective to inhibit or reduce development of an autism spectrum disorder in a fetus or an infant.

Also provided is a method of determining the likelihood that a fetus or infant of a pregnant prospective mother will present with an autism spectrum disorder comprising quantifying the levels of antibodies directed to one or more of Caspr2, KCNAB2, KCNAB1, EDIL3, IVD, SULT4A1, TNIP2, RAI16 or GDP D5 in a sample obtained from the mother's blood and comparing each quantified level to a predetermined control level for that respective antibody, wherein an increased titer of antibody or antibodies for one or more of Caspr2, KCNAB2, KCNAB1, EDIL3, IVD, SULT4A1, TNIP2, RAI16 or GDP D5 indicates an increased likelihood of the fetus or infant of a pregnant prospective mother will present with an autism spectrum disorder.

Additional objects of the invention will be apparent from the description which follows.

DETAILED DESCRIPTION OF THE INVENTION

Figures 1A, 1B:
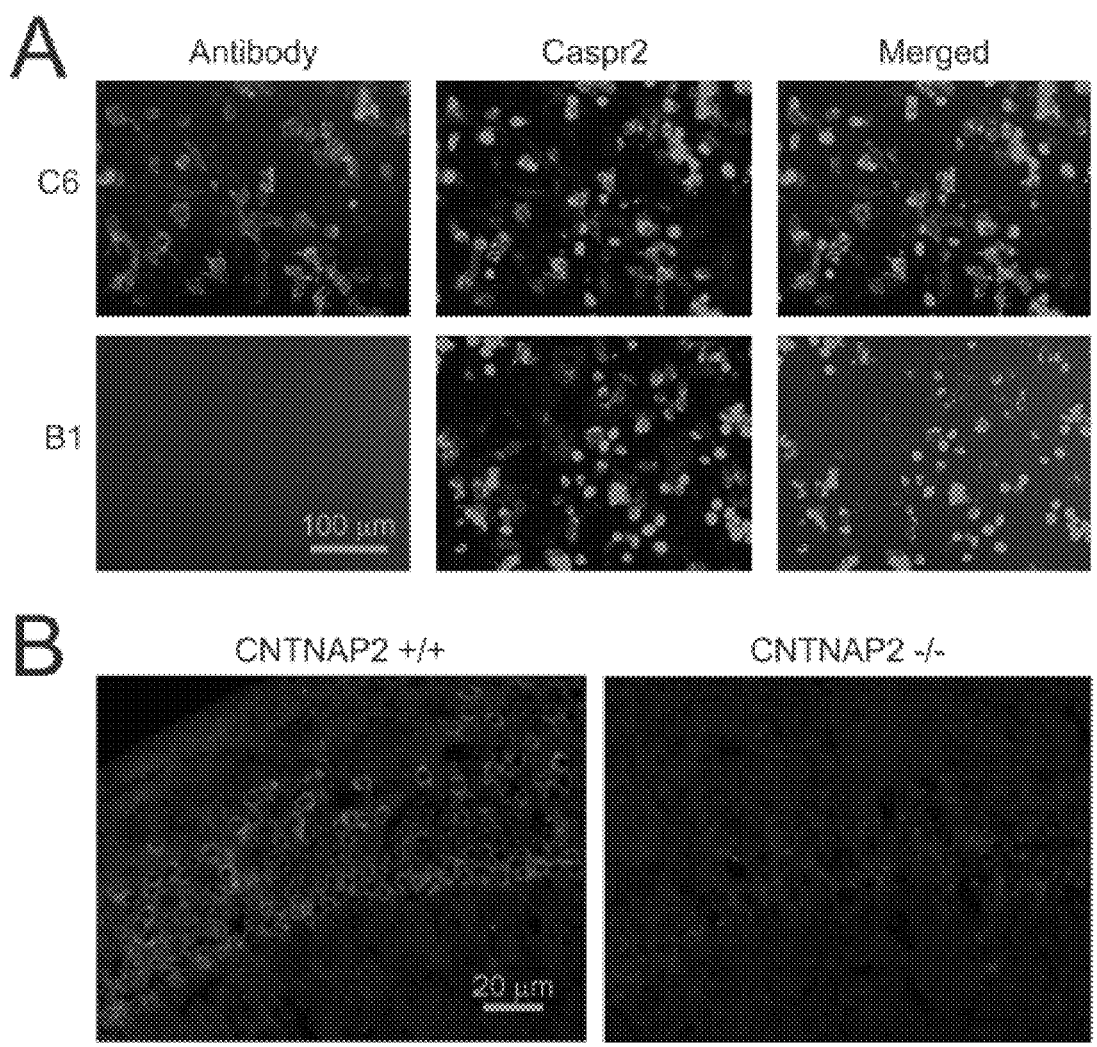
FIG. 1A-1B: Brain-reactive monoclonal antibody C6 binds to Caspr2. (1A) C6 (top left panel), but not B1-control (bottom left panel), binds Caspr2 on live HEK 293T cells, expressing tGFP-Caspr2 (middle panel). No staining was seen on cells expressing only tGFP or non-transfected cells (data not shown) (1B) Reduced binding of brain-reactive C6 to the CA1 region in the hippocampus of CNTNAP2−/− mice.

A method is provided for inhibiting or reducing development of an autism spectrum disorder in a fetus or an infant comprising administering to a mother pregnant with the fetus or prior to the fetus being born as an infant while the mother is pregnant, an amount of an agent which binds an antibody directed to Caspr2, KCNAB2, KCNAB1, endothelial integrin ligand (EDIL3), IVD, brain specific sultatransferase (SULT4A1), TNIP2, retinoic acid induced 16 (RAI16) or GDP D5, effective to inhibit or reduce development of an autism spectrum disorder in a fetus or an infant. In an embodiment, the Caspr2, KCNAB2, KCNAB1, EDIL3, IVD, SULT4A1, TNIP2, RAI16 and GDP D5 is human Caspr2, KCNAB2, KCNAB1, EDIL3, IVD, SULT4A1, TNIP2, RAI16 and GDP D5, respectively. In an embodiment of the method the agent comprises a peptide comprising the sequence of an extracellular portion of a Caspr2, KCNAB2, KCNAB1, EDIL3, IVD, SULT4A1, TNIP2, RAI16 or GDP D5. In an embodiment, the peptide is made from all D amino acids.

A method is also provided for inhibiting or reducing development of an autism spectrum disorder in a fetus or an infant comprising extracorporeally contacting blood of a mother pregnant with the fetus or prior to the fetus being born as an infant while the mother is pregnant, with an amount of an agent which binds an antibody directed to Caspr2, KCNAB2, KCNAB1, endothelial integrin ligand (EDIL3), IVD, brain specific sultatransferase (SULT4A1), TNIP2, retinoic acid induced 16 (RAI16) or GDP D5 so as to reduce the blood levels of an antibody directed to Caspr2, KCNAB2, KCNAB1, EDIL3, IVD, SULT4A1, TNIP2, RAI16 or GDP D5, and recirculating the blood so treated back into the mother effective to inhibit or reduce development of an autism spectrum disorder in a fetus or an infant.

In an embodiment of the methods comprising extracorporeally contacting the blood, the agent can be fixed to a support. In aseptic conditions, the blood can be run over or through the support so as to reduce levels of antibody directed to Caspr2, KCNAB2, KCNAB1, EDIL3, IVD, SULT4A1, TNIP2, RAI16 and/or GDP D5 in the blood and then the blood is returned to the mother. In an embodiment, the blood levels of an antibody directed to Caspr2, KCNAB2, KCNAB1, EDIL3, IVD, SULT4A1, TNIP2, RAI16 or GDP D5 are reduced by hemofiltration. In an embodiment, the blood levels of an antibody directed to Caspr2, KCNAB2, KCNAB1, EDIL3, IVD, SULT4A1, TNIP2, RAI16 or GDP D5 are reduced by hemoadsorption. In an embodiment, the blood levels of an antibody directed to Caspr2, KCNAB2, KCNAB1, EDIL3, IVD, SULT4A1, TNIP2, RAI16 or GDP D5 are reduced by plasma filtration.

In an embodiment of the methods, the agent binds an antibody directed to KCNAB2.

In an embodiment of the methods, the agent binds an antibody directed to EDIL3.

In an embodiment of the methods, the agent binds an antibody directed to IVD.

In an embodiment of the methods, the agent binds an antibody directed to SULT4A1.

In an embodiment of the methods, the agent binds an antibody directed to TNIP2.

In an embodiment of the methods, the agent binds an antibody directed to RAI16.

In an embodiment of the methods, the agent binds an antibody directed to GDP D5.

In an embodiment of the methods, the agent binds an antibody directed to KCNAB1.

In an embodiment of the methods, the agent binds an antibody directed to Caspr2.

In an embodiment of the methods, the Caspr2, KCNAB2, KCNAB1, EDIL3, IVD, SULT4A1, TNIP2, RAI16 or GDP D5 is human.

In an embodiment of the methods, the agent comprises a fusion protein which comprises a peptide comprising the sequence of an extracellular portion of a Caspr2, KCNAB2, KCNAB1, EDIL3, IVD, SULT4A1, TNIP2, RAI16 or GDP D5.

In an embodiment of the methods, the fusion protein also comprises an immunoglobulin Fc sequence. In an embodiment of the methods, the immunoglobulin is an IgG. In an embodiment of the methods, the IgG is an IgG1. In an embodiment of the methods, the IgG is an IgG2. In an embodiment of the methods, the IgG is an IgG3. In an embodiment of the methods, the IgG is an IgG4. In an embodiment of the methods, the immunoglobulin is an IgM.

In one embodiment of the methods, a fusion protein as used herein means a fusion protein constructed of a portion of an immunoglobulin and an extracellular portion of a Caspr2, KCNAB2, KCNAB1, EDIL3, IVD, SULT4A1, TNIP2, RAI16 or GDP D5, or a protein having an identical sequence thereto. In an embodiment, the Caspr2, KCNAB2, KCNAB1, EDIL3, IVD, SULT4A1, TNIP2, RAI16 or GDP D5 has the sequence of a human Caspr2, KCNAB2, KCNAB1, EDIL3, IVD, SULT4A1, TNIP2, RAI16 or GDP D5, respectively. In an embodiment, the portion of an immunoglobulin is a portion of an IgG or an IgM. In an embodiment, it as a portion of an IgG. The IgG portion of the fusion protein can be, e.g., any of an IgG1, IgG2, IgG2a, IgG2b, IgG3 or IgG4 or a portion thereof. In an embodiment, the portion is an Fc sequence (the sequence of a whole Fc region). In an embodiment the fusion protein comprises a sequence identical to an Fc portion of a human IgG1, human IgG2, human IgG2a, human IgG2b, human IgG3 or human IgG4. In an embodiment the fusion protein comprises a sequence identical to an Fc portion of a human IgG1.

In an embodiment, the Fc domain has the same sequence or 95% or greater sequence similarity with a human IgG1 Fc domain. In an embodiment, the Fc domain has the same sequence or 95% or greater sequence similarity with a human IgG2 Fc domain. In an embodiment, the Fc domain has the same sequence or 95% or greater sequence similarity with a human IgG3 Fc domain. In an embodiment, the Fc domain has the same sequence or 95% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH.

In an embodiment of the methods, the fusion protein comprises an immunoglobulin Fc sequence having the same sequence as a human Ig Fc sequence. Immunoglobulin Fc sequences are well known in the art. In an embodiment, the term "Fc sequence" herein is used to define a C-terminal region of an immunoglobulin heavy chain, including native sequence Fc regions and variant Fc regions. Although the boundaries of the Fc sequence of an immunoglobulin heavy chain might vary, the human IgG heavy chain Fc is usually defined to stretch from an amino acid residue at position Cys226, or from Pro230, to the carboxyl-terminus thereof. In an embodiment, the C-terminal lysine of the Fc may be removed, for example, during production or purification, or by recombinantly engineering the nucleic acid encoding a heavy chain of the antibody.

In a fusion protein, the presence of the Fc domain markedly increases the plasma half-life of the attached protein, which prolongs therapeutic activity. In addition, the Fc domain also enables the fusion protein to interact with Fc-receptors. In an embodiment, the fusion protein comprises a Caspr2, KCNAB2, KCNAB1, EDIL3, IVD, SULT4A1, TNIP2, RAI16 or GDP D5 portion linked to an Fc domain. In an embodiment, the Caspr2, KCNAB2, KCNAB1, EDIL3, IVD, SULT4A1, TNIP2, RAI16 or GDP D5 portion is bound directly by a peptide bond to the Fc domain. In an embodiment of the methods, the Caspr2, KCNAB2, KCNAB1, EDIL3, IVD, SULT4A1, TNIP2, RAI16 or GDP D5 portion is linked to the Fc domain through a linker. In an embodiment the Caspr2, KCNAB2, KCNAB1, EDIL3, IVD, SULT4A1, TNIP2, RAI16 or GDP D5 portion is an extracellular portion. In an embodiment, it is linked via a peptide linker which permits flexibility. In an embodiment, the linker is rigid. In an embodiment the linker is cleavable. Non-limiting examples of flexible linkers within the scope of the invention are Gn, and GGGGS, and (GGGGS)n where n=2, 3, 4 or 5. Non-limiting examples of rigid linkers within the scope of the invention are (EAAAK)n, (XP)n. Non-limiting examples of cleavable linkers within the scope of the invention include disulfide links and protease cleavable linkers. In a preferred embodiment, the linker is a peptide linker.

The Fc sequences of the fusion proteins described herein may be mutated. Preferred embodiments include K322A and N297D human IgG1 Kabat numbering. The mutations K322A and N297D showed limited (reduced) transplacental transfer. The mutation K322A is based on standard Kabat numbering of the Fc AA's 75-53.K322A.HC1f—the Lysine at position 322 is mutated to Alanine. The mutation N297D is based on the standard Kabat numbering of the Fc AA's 75-53.N297D.HC1f—the Asparagine at position 297 is mutated to Aspartate. In contrast, P329A (a mutation of Proline at position 329 to Alanine) showed the same transplacental transfer as test antibodies—e.g. AQP4 IgG, on neonatal Fc receptor (FcRn) binding.

In an embodiment, the fusion protein described herein is recombinantly produced. In an embodiment, the fusion protein is produced in a eukaryotic expression system. In an embodiment, the fusion protein produced in the eukaryotic expression system comprises glycosylation at a residue on the Fc portion.

In an embodiment, the fusion protein is a homodimer. In an embodiment, the fusion protein is monomeric. In an embodiment, the fusion protein is polymeric.

In an embodiment of the methods, the agent comprises a plasma-soluble peptide which comprises the sequence of an extracellular portion of a Caspr2, of a KCNAB2, of a KCNAB1, of an EDIL3, of an IVD, of a SULT4A1, of a TNIP2, of an RAI16 or of a GDP D5.

In an embodiment of the methods, the mother or the fetus has been diagnosed as at risk for an autism spectrum disorder in the fetus by a method comprising obtaining a sample from the mother's blood and quantifying the level of antibody directed to Caspr2, KCNAB2, KCNAB1, EDIL3, IVD, SULT4A1, TNIP2, RAI16 or GDP D5 in the sample, and comparing the level so quantified to a predefined control level of the respective antibody, wherein an antibody level in the sample in excess of the control level has been determined, so diagnosing the mother, or fetus, as at risk for an autism spectrum disorder in the fetus.

In general, the amount of an agent "effective" (e.g., a therapeutic agent, composition, and/or formulation such as the agent or a composition comprising the agent) is an amount effective to achieve a stated effect, to elicit the desired biological response. In some embodiments, a therapeutically effective amount of a substance is an amount that is sufficient, when administered to a pregnant mother to reduce the likelihood or extent of an autism spectrum disorder in the fetus of the pregnant mother or the infant born from the pregnant mother. As will be appreciated by those of ordinary skill in this art, and effective amount of a substance may vary depending on such factors as the desired biological endpoint, the substance to be delivered, the pharmacokinetics of the compound, the target cell or tissue, the disease being treated, the mode of administration, and the patient, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Those of ordinary skill in the art will appreciate that, commonly, an effective amount will be administered over a series of individual doses. In some embodiments, the term "effective amount" when used in a pharmaceutical context (e.g., pharmaceutically effective amount) means that an agent is present in an amount sufficient to achieve a desired therapeutic effect.

Routes of administration to the mother encompassed by the methods of the invention include, but are not limited to, each of the following individual routes, and any subset thereof, auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intraplacental, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, uretheral, and vaginal administration.

In an embodiment of the methods, the method further comprises an initial step of receiving identification of the mother as being at risk for an autism spectrum disorder in a fetus she is pregnant with and administering the amount of an agent to the mother so identified. In an embodiment, wherein the mother as identified as not being at risk for an autism spectrum disorder in a fetus she is pregnant with the mother is not administered the amount of an agent.

Also provided is a method of determining the likelihood that a fetus or infant of a pregnant prospective mother will present with an autism spectrum disorder comprising quantifying the levels of antibodies directed to one or more of Caspr2, KCNAB2, KCNAB1, EDIL3, IVD, SULT4A1, TNIP2, RAI16 or GDP D5 in a sample obtained from the mother's blood and comparing each quantified level to a predetermined control level for that respective antibody, wherein an increased titer of antibody or antibodies for one or more of Caspr2, KCNAB2, KCNAB1, EDIL3, IVD, SULT4A1, TNIP2, RAI16 or GDP D5 indicates an increased likelihood of the fetus or infant of a pregnant prospective mother will present with an autism spectrum disorder.

As used herein, a predetermined control level is a value decided or obtained, usually beforehand, as a control. The concept of a control is well-established in the field, and can be determined, in a non-limiting example, empirically from non-afflicted subjects (versus afflicted subjects), and may be normalized as desired (in non-limiting examples, for volume, mass, age, location, gender) to negate the effect of one or more variables.

In an embodiment of the methods, the subject is human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL RESULTS

Introduction

Autism spectrum disorder (ASD) occurs in 1 in 67 births and rising, at a disabling financial and emotional cost. Advances in the understanding of pathobiological mechanisms implicate maternal brain-reactive antibodies in ASD development.

Maternal antibody can enter the fetal brain (7) and brain-reactive antibody can affect fetal brain development and lead to cognitive impairment in the offspring (8). This laboratory, and others, have shown that mothers of ASD children have significantly more circulating antibodies that are reactive to brain antigens as compared to unselected women of child bearing age or mothers of a typically developing child (9, 10). Intravenous administration of serum or selected brain antigen specific antibodies to pregnant mice or monkeys causes neurodevelopmental and behavioral defects in the offspring (11, 12).

Understanding this mechanism requires isolation and study of monoclonal antibodies and identification of the specific brain antigenicity. A monoclonal antibody (designated C6) was isolated that binds contactin-associated protein-like 2 (Caspr2), a component of the Kv1 potassium channel and necessary for membrane stability of AMPA and NMDA receptors. Elevated titers of these specific antibodies were observed in seropositive mothers of an ASD child. To demonstrate their contribution to ASD, mice were exposed in utero to maternal C6. This mediated abnormal cortical development with decreases in inhibitory neurons and decreased dendritic complexity of excitatory neurons in the hippocampus of male offspring and associated impairments in social preference, flexible learning, and increased repetitive behavior. These results demonstrate that a monoclonal antibody in maternal circulation can mediate brain abnormalities that have been associated with ASD.

Example 1

Monoclonal antibodies were generated from blood samples of mothers of children with ASD who were previously shown to have brain-reactive polyclonal antibodies. Because these blood samples were obtained years after the birth of the affected child, memory (CD27+) B cells that were reactive against antigens present in a human fetal brain lysate were focused on. To enable detection of these cells, human fetal brain lysate fragments were biotinylated and incubated with B cells. Individual CD19+ CD27+ B cells that bound fetal brain fragments, detected by streptavidin binding were isolated. Immunoglobulin heavy and light chain variable region genes were amplified by PCR and expressed in vitro in human embryonic kidney cells (HEK 293) as IgG1, κ antibodies (13).

Several antibodies that bound mouse brain at 5 μg/ml in an immunohistology assay (9) were identified. Two platforms were used to determine the antigenic specificity of these antibodies: a human antigen array containing 9,000 proteins (Invitrogen) and a cell-based assay for reactivity to antigens previously shown to be important in ASD. A monoclonal antibody was studied that we termed C6 that binds the extracellular portion of Caspr2 (FIG. 1A), a component of the voltage gated Kv1 potassium channel (14). Caspr2 is a transmembrane protein that stabilizes the channel on the cell membrane of neurons (15). Caspr2 is present at the soma, axon and dendrites spines, (14, 16) and its expression in the brain begins during fetal development [data not shown, also in (14, 17)].

Immunohistochemical analysis revealed significantly enhanced binding of C6 to brain sections of wildtype mice compared to brain sections of mice with a deletion of CNTNAP2, the gene that encodes Caspr2 (FIG. 1B), confirming its specificity for Caspr2. Importantly, the serum of the woman from whom C6 was derived displayed diminished, but not absent, binding to CNTNAP2−/− mouse brain.

Figures 2A, 2B, 2C, 2D:
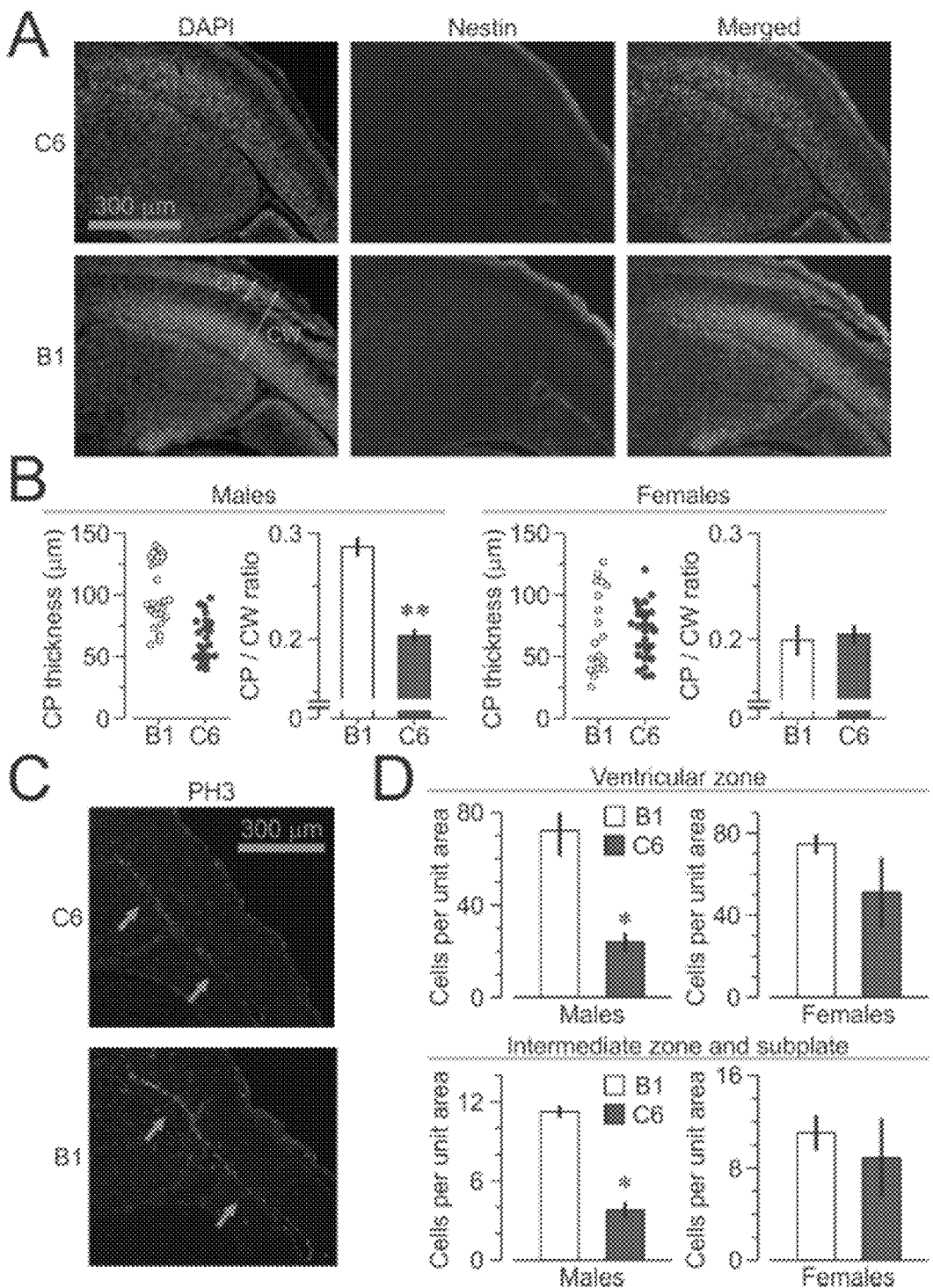
FIG. 2A-2D: Prenatal cortical abnormalities in the C6-exposed fetus. (2A) Nestin staining shows a thin cortical plate (CP) in C6-compared to B1-exposed male brains. (2B) CP and CP: cortical width (CW) ratio in male and female fetal brain. **$P<0.0001$, $t=7.15$, t test. (2C) PH3+ staining shows fewer mitotic cells in the C6-exposed. Arrows identify regions of neurogenesis in the ventricular zone (VZ). (2D) Quantification of PH3+ in the VZ, Intermediate zone (IZ) and sub-plate (SP). Unit area=62.5 mm$^2$.
*$P<0.05$, $Z=2.34$, Mann Whitney test. (B,D) Number of mice: B1=5, C6=4, 2 litters for each antibody.

To determine the pathogenic potential of the C6 monoclonal antibody, it was administered intravenously (200 µg) to female mice on day E13.5 of pregnancy, a time when antibody crosses the placenta and can still penetrate fetal brain tissue (7) and when Caspr2 is transcribed in the brain (14, 17). As a control, B1 was used, a human monoclonal antibody previously shown not to affect fetal brain development (18). Male fetuses from dams sacrificed 2 days after initial exposure to C6 exhibited a thinned cortical plate; this abnormality was not observed in female fetuses nor was it present in male or female fetuses exposed to B1 (FIG. 2A,B). In accordance with a previous report showing that the male cortical plate post partum is thicker than the female cortical plate (19), a thicker cortical plate was observed in male compared to female fetuses exposed to B1 antibody. Male fetuses exposed to C6 also exhibited a decrease in mitotic cells in the developing cortex, compared to male fetuses exposed to B1; this abnormality was not observed in C6-exposed female fetuses (FIG. 2C,D).

Figures 3A, 3B, 3C, 3D, 3E, 3F:
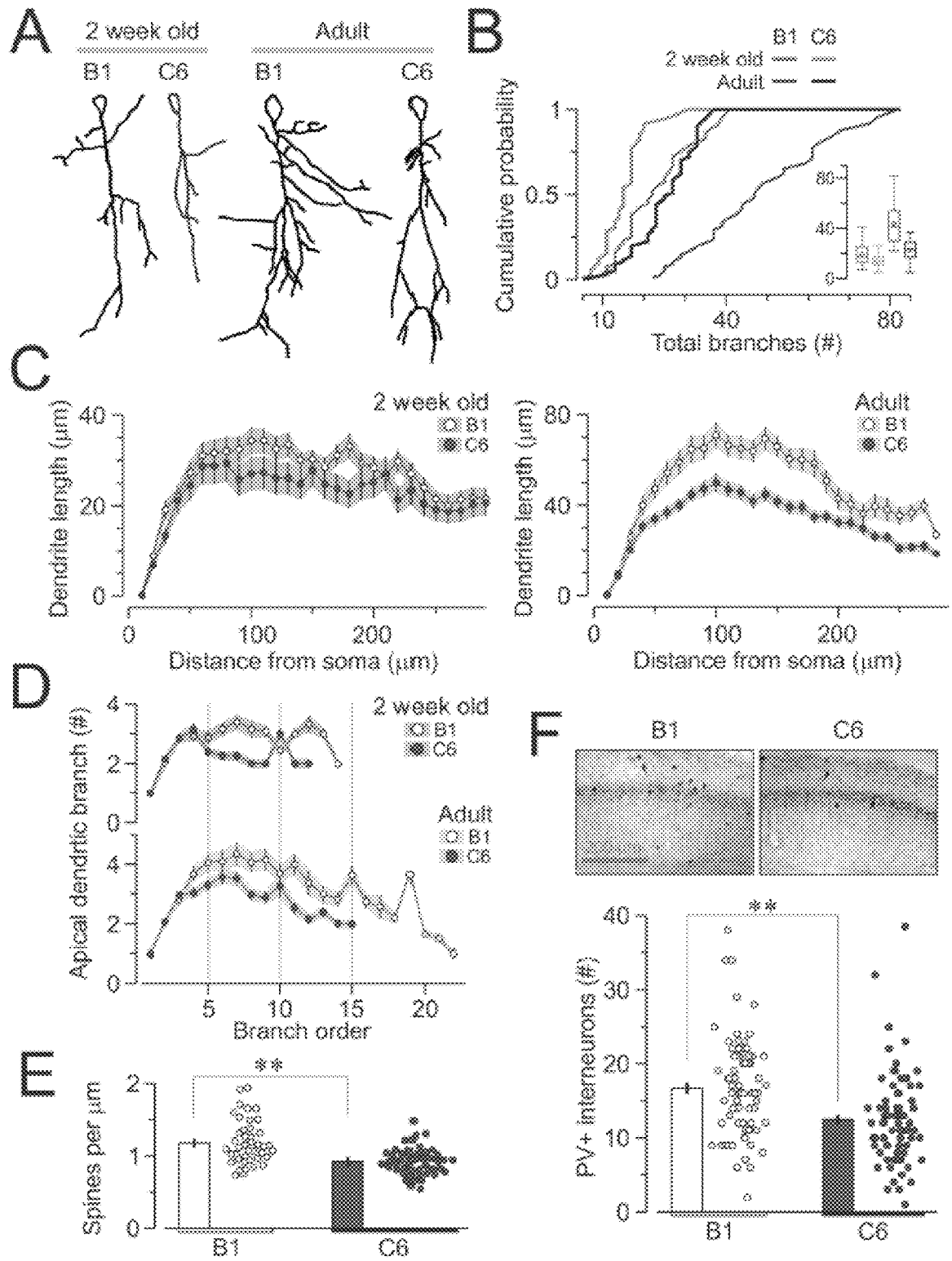
FIG. 3A-3F: Postnatal hippocampal CA1 abnormalities in C6-exposed male mice. (3A-3E) CA1 pyramidal neurons of C6-exposed mice show reduced dendritic length and spine density. Analysis includes: 2 week old mice (n=3 per group); Neurons: B1=45, C6=49, and adult animals (n=4 per group); Neurons: B1=70, C6=83. Each group includes animals from 2 litters. (3A) Traced drawings of representative Golgi-impregnated CA1 pyramidal neurons from 2 week old (left) and adult (16-20 week old) (right) B1- and C6-exposed mice. (3B) Cumulative probability of total number of branches. 2 week old B1 vs C6, $P<0.003$, $D=0.35$, Kolmogorov-Smirnov (KS) test; adult, $P<0.001$, $D=0.64$, KS test. Insert, box plot, represents total number of branches, with data presented as mean and quartiles. (3C) Scholl analysis depicts dendritic length as a function of distance from the soma. Left: 2 week old mice, $P<0.005$, $D=0.44$, KS. Right: adult mice, $P<0.001$, $D=0.97$, KS test. (3D) Number of dendritic branches as a function of branch order, centrifugally defined to start at the origin of the tree and continue out towards the termination, and as the number of segments traversed from the origin. The C6- and B1-exposed mice differ significantly at both ages: 2 week old, $P<0.01$, $D=0.6$, KS test; adult, $P<0.03$, $D=0.45$, KS test. (3E) Reduced density of synaptic dendritic spines in CA1 neurons in C6-exposed mice; B1=1.18±0.04 spines/μ; C6=0.92±0.02 spines/μ; P<0.001, t=4.78, t test (3F) Top, representative photomicrographs of the CA1 field showing labeled PV+ interneurons. Bottom, quantification of PV+ neurons in adult B1 (n=1251) and C6 (n=998) groups, P<0.001 Z=4.25 Mann-Whitney, 4 animals per group, 2 litters.

Brains of male mice that had experienced in utero exposure to C6 or B1 were analyzed at 16-20 weeks of age. Assessment of cresyl violet stained brain sections showed no major alteration in brain structures. A higher resolution analysis showed that hippocampal neurons of C6-exposed mice exhibited fewer dendritic processes and dendritic spines, and less dendritic branching than hippocampal neurons of B1-exposed mice (FIG. 3A-E). Hippocampal CA1 neurons are not fully developed until ~4 weeks of age, and that prior to that time, they have reduced dendritic length and branching (20). To assess the time course of the structural lesion, CA1 neurons in 2 week old mice were examined. CA1 neurons from B1-exposed 2 week old mice showed immature dendritic architecture when compared to B1-exposed 8 week old mice. The 2 week old C6-exposed mice exhibit reduced apical dendritic branches, and the adult C6-exposed mice show a similar number of branches as the B1-exposed 2 week old mice (FIG. 3B-D). Interestingly, downregulation of Caspr2 in cultured neurons leads to a decrease in dendritic processes in vitro (21).

GABAergic parvalbumin positive (PV+) neurons were also stained for in adult male mice exposed in utero to C6 or B1. A reduction in PV+ neurons was observed in the CA1 region of the hippocampus in C6-exposed male mice (FIG. 3F), consistent with the report that CNTNAP2−/− mice exhibit a 20% reduction in the number of GABAergic PV+ interneurons in the hippocampus.

To examine the potential effect of in utero exposure to C6 on behavior, mice exposed to C6 or B1 in utero were studied as adults in a variety of tasks that focus on core symptoms of ASD (22). C6-exposed mice of either sex did not demonstrate sickness behavior, or alterations in weight, coat, grip strength, body tone or reflexes, unsupervised locomotion (P>0.4, t test n=17, 5 litters) or anxiety measured in the open field test (P>0.8, ANOVA n=17, 5 litters).

Figures 4A, 4B, 4C:
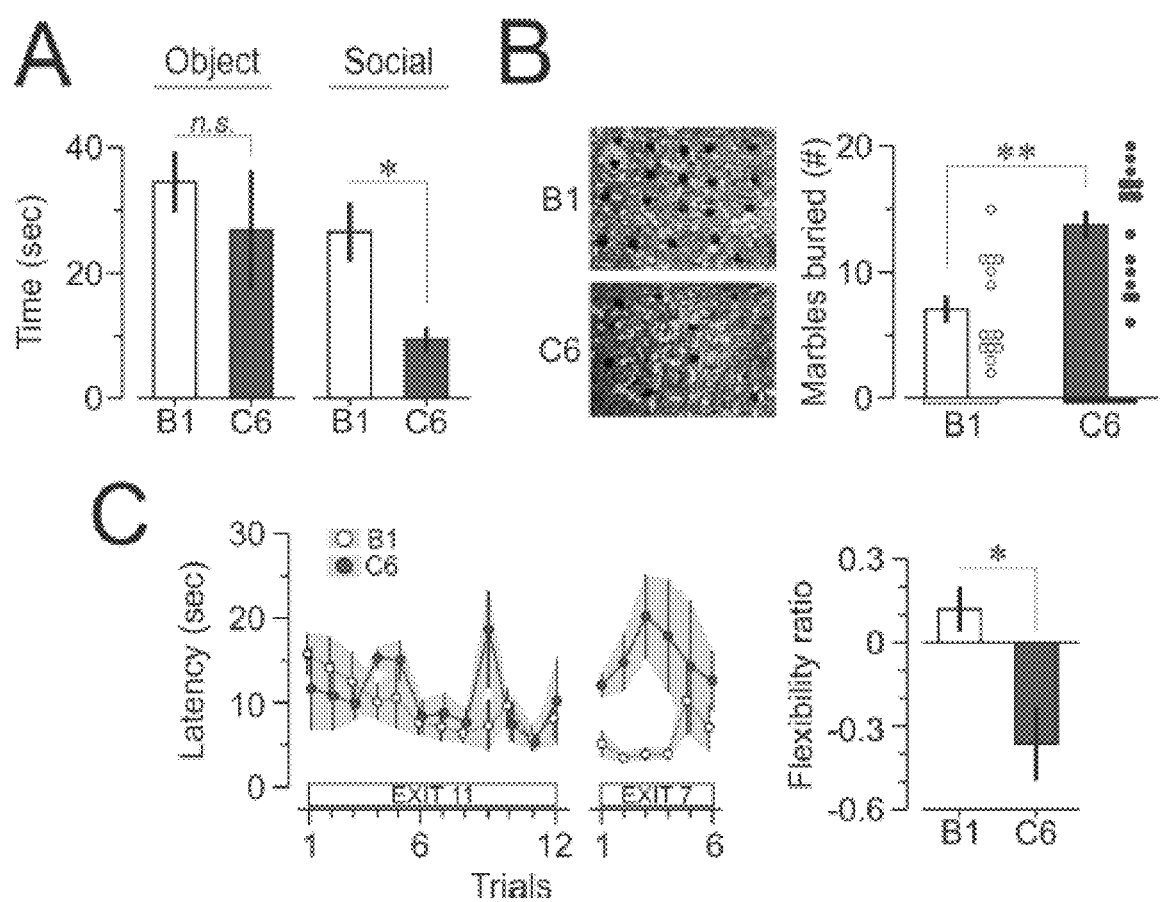
FIG. 4A-4C: Impaired performance of C6-exposed male offspring in tasks that resemble core ASD symptoms. Maternal antibody-exposed male mice were subjected to behavioral assessment at adulthood (10-14 weeks). (4A) Social preference task. Left columns (object), C6-exposed mice (n=15) examine a novel object for a similar amount of time as mice in the B1 group (n=15); Right columns (social), C6-exposed mice spend significantly less time near an unfamiliar mouse, showing impaired social preference; *P<0.005, t=3.2, t test; 4-5 litters per group. (4B) Marble burying task. Left, representative examples of burying patterns in the two groups. Right, C6-exposed mice (n=14) display enhanced stereotypic behavior because they bury more marbles than the B1 group (n=15); **P<0.0005, t=4.2, t test; 4-5 litters per group. (4C) Clock maze task. Left, the graph shows the latency to escape from the center of the maze to a peripherally located exit. C6-exposed mice (n=6) perform similarly to B1-exposed mice (n=11) in the initial phase (Exit 11) but are impaired in the second phase, when learning a different location (Exit 7). Right, the flexibility ratio (defined in Methods) shows that C6-exposed mice are significantly less likely to switch from a familiar exit to a novel one, showing impaired flexible learning; *P<0.02, Z=2.36, Mann Whitney test; 2-3 litters per group.

Male mice exposed to C6 spent significantly less time in proximity to another mouse in the social preference test, but spent similar amounts of time as B1-exposed mice in proximity to a novel object (FIG. 4A). Moreover, C6-exposed mice buried significantly more marbles than B1-exposed mice in the marble burying test that measures stereotypic or compulsive behavior (FIG. 4B). They were also impaired at learning a new exit location in the clock maze but showed normal learning in the initial task, thereby exhibiting a defect in flexible learning (FIG. 4C). In contrast, female offspring exposed in utero to either C6 or B1 performed equivalently in all tasks, confirming the histologic developmental data showing no effect of antibody on the female fetal brain.

To determine the frequency of antibodies with this specificity in a population of women with a child with ASD, plasma from mothers of children with ASD that had previously been shown to have brain-reactive serology (9) was examined. Thirty-seven percent (20 of 53) of plasma samples bound to the cell membrane of non-permeabilized Caspr2-transfected HEK 293T cells, while only 12% (8 of 63) of samples from mothers of an ASD child lacking brain-reactive antibodies and 12% (6 of 51) of samples from unselected women of child-bearing age exhibited such reactivity (P<0.001, chi-square test).

These results directly establish that some mothers of a child with ASD express antibodies that bind fetal brain antigens in vivo. C6 which has specificity for Caspr2 mediates abnormal fetal brain development and results in long term behavioral impairments. As the fetal blood-brain barrier is porous to antibodies (7), pathogenic autoantibodies present in the mother's blood can affect the developing brain even in the absence of detectable disease in the mother. This paradigm in which maternal antibodies affect fetal brain development with long term cognitive effects has already been reported in systemic lupus (18, 23), in which exposure to NMDA-receptor-reactive autoantibodies in utero led to abnormal fetal brain development and persistent neurocognitive deficits (18).

A rare variant of CNTNAP2, the gene that encodes Caspr2, is associated with ASD (24). Families with mutant CNTNAP2, the gene encoding Caspr2, display epilepsy (25), obsessive compulsive behaviors (26) and variable, gender-dependent structural abnormalities in the brain (27). Mice with a deletion of CNTNAP2 display disrupted neuronal migration, a loss of inhibitory GABAergic neurons and behavioral characteristics which are considered to represent an ASD-like phenotype in mice, such as hyperactivity, stereotypic behaviors, reduced flexible learning in the Morris water maze and social preference abnormalities (17). During development, Caspr2 is highly expressed in the ventricular proliferative zones (14, 17), and mice lacking Caspr2 show neuronal migration impairments. Interestingly, changes in the cortical thickness as well as decreased neuronal packing (28) have been observed in ASD. It is possible that cortical thinning and the reduced number of proliferating cells are mediated indirectly by another protein known as Transient Axonal Glycoprotein-1 (TAG1), which co-localizes with Caspr2 (15) and has a role in the migration of proliferating neurons in the cortex.

It was also found that adult mice that were exposed in utero to C6 showed reduced dendrite arborization in the hippocampus. The data suggest that in adulthood, these mice exhibit a similar level of dendrite complexity as B1 control mice at 2 weeks of age. A reduction in GABAeric PV+ neurons in the hippocampus was also observed. In parallel, impairments were observed in social preference and flexible learning and increased stereotypic behavior. These behaviors are recognized to involve the cortico-striatal circuit and are sensitive to hippocampal input (29, 30).

The fact that only male mice exposed in utero to C6 antibody exhibited neurodevelopmental abnormalities is of particular interest given the strong male bias in ASD (31). The inventors are not aware of any other reports addressing a gender bias in mouse models of ASD. Nevertheless, male gender was an important factor in the linkage association between CNTNAP2 and impaired language development in a human genealogy (24). Antibodies with Caspr2 specificity appear to be frequent in mothers of an ASD child.

Example 2

A unique human blood resource (Simons Simplex Collection, Autism Genetic Resources and GAP registry at The Feinstein Institute for Medical Research) was utilized to demonstrate that the frequency of anti-brain antibodies is significantly higher in the blood of mothers of children with ASD (11%) relative to control groups (2%, p<0.0001). Brain-reactive monoclonal antibodies were identified and single cell cloned from mothers of ASD children (single cell expression cloning of IgG domains from cell-sorted memory B cells). In brief, isolated B cells from peripheral blood were incubated with human fetal brain lysate previously labeled with biotin and B cell-brain antigen complexes were isolated using avidin chromatography. Because the blood was obtained years after the pregnancy that resulted in a child with ASD, it was reasoned that only B cells in the memory compartment would be of interest. Fortunately, such memory B cells persist in humans for years to decades and thus can provide a window on autoreactivity that may have been present during a pregnancy occurring years before. Accordingly, the next step used fluorescent markers and flow cytometry to sort individual memory B cells into single wells. Using the technique first described by Nussenzweig and coworkers, IgG heavy and light variable regions were cloned into human constructs (34). These were then sequenced and cotransfected into HEK 293T cells for expression. Immunoreactivity to brain was validated using immunohistochemistry to fetal and adult mouse brain and monoclonal antibodies of interest were expressed and purified with Protein G chromatography. A library of 20 brain-reactive monoclonal antibodies was generated. Consistent with the selection of memory B cells, most of these monoclonals comprise extensive somatic hypermutation of the variable regions, a feature of B cells that have matured through a germinal center response and have entered a memory cell compartment. Putative antigens were identified by screening pooled antibody preparations on full length human protein arrays followed by immunoblots for select antibodies.

Of 20 such brain-reactive monoclonal antibodies, 8 were determined to react against targets known to be involved in neurodegenerative diseases (KCNAB2, KCNAB1, EDIL3, IVD, SULT4A1, TNIP2, RAI16 or GDP D5). Of these 8 putative antigens, all are present on proteins involved in neurodegenerative diseases and 4 are present on subunits of a single protein complex—a potassium voltage-gated channel (2 monoclonals bind KCNAB1 and 2 bind KCNAB2). Moreover, sequence analysis indicates that the 2 anti-KCNAB2 antibodies utilize identical heavy chains. These findings are especially provocative since the kcnab2 gene has been implicated with ASD in a Genome Wide Association Study (GWAS).

Figure 5:
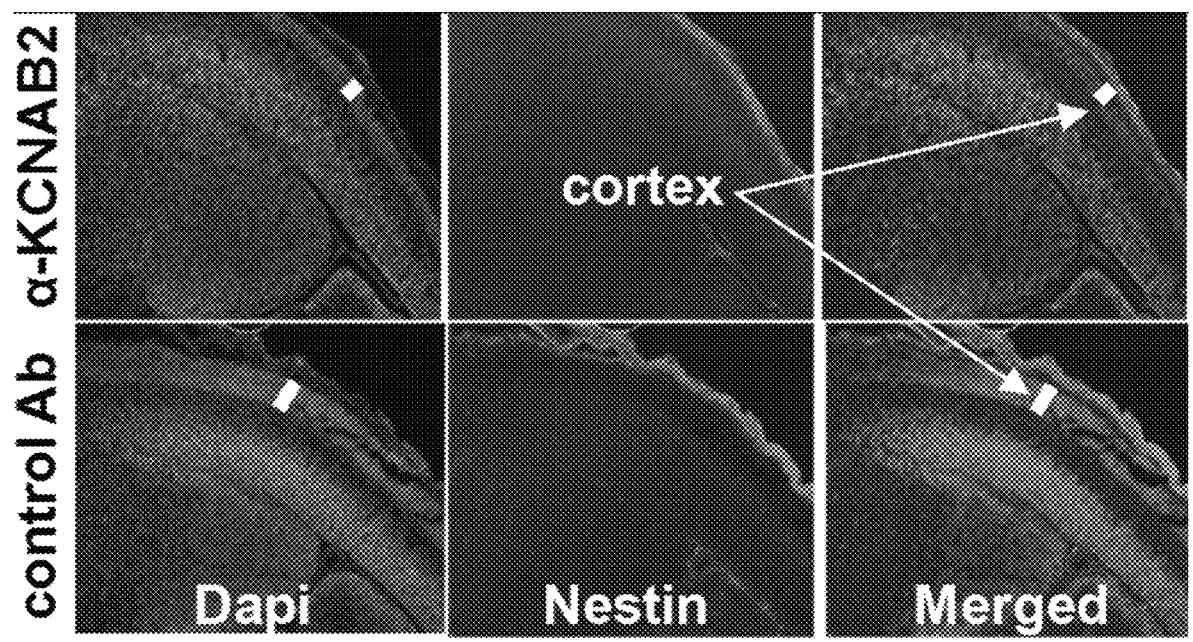
FIG. 5: Fetuses exposed to anti-KCNAB2 monoclonal antibodies have a thin cortex. Anti-KCNAB2 (top) or non-brain reactive control antibody (bottom) was injected into pregnant mice (E13.5) and fetuses were harvested 36 hr later and processed to stain nuclei (Dapi), nestin or both (merged). Cortex thickness is indicated with white bars.
Figure 6:
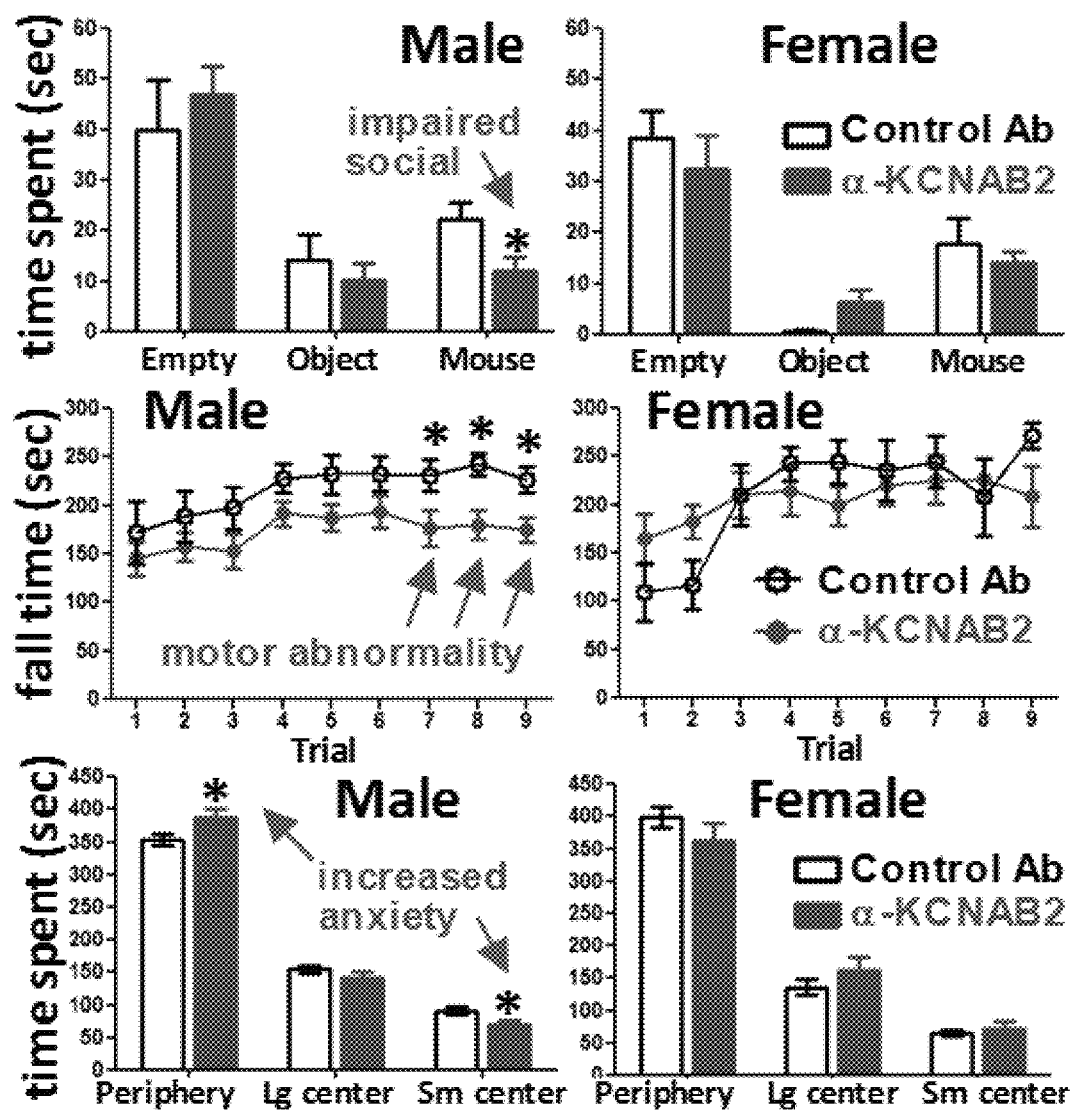
FIG. 6: A brain-reactive monoclonal Ab cloned from a mother of an ASD child elicits ASD-like behavior. Anti-KCNAB2 (maroon) or non-brain reactive control antibody (black) was injected into pregnant mice (E13.5) and off-spring were analyzed for social preferences (top histograms), motor abnormalities (middle graphs) or anxiety (bottom histograms) at adulthood. Note that male (left graphs) but not female (right graphs) offspring display ASD-related behavior.

When injected intravenously in pregnant mice on day E13.5, one human anti-KCNAB2 monoclonal antibody leads to abnormal cortical development and behavioral abnormalities in male but not female offspring. For these studies, the pregnant mice contained 13.5 day old fetuses—a developmental stage when brain structures implicated as relevant for ASD are being formed. When analyzed 36 hr following antibody administration, fetuses from mice injected with non-brain-reactive control IgG displayed normal histology. In contrast, the fetuses of mice injected with C6 anti-KCNAB2 IgG displayed an abnormally thin brain cortical layer (FIG. 5), consistent with the antibodies penetrating the fetal brain. Parallel phospho-histone 3 staining at this time window indicates significantly fewer mitotic cells in the fetuses exposed to anti-KCNAB2 antibody (not shown). Finally when analyzed as adults (10-14 wk), both male and female offspring from pregnant mice injected with non-brain-reactive control IgG displayed normal behavior when assessed using a variety of mouse ASD behavioral phenotyping assays (e.g., anxiety, motor, social; FIG. 6). Strikingly, parallel behavioral assays performed on adult offspring of mice injected with anti-KCNAB2 IgG revealed gender-specific abnormalities: only male (FIG. 6, left) but not female (FIG. 6, right) offspring display ASD-related behavior in all three standard ASD behavioral assays (social preference, rotorod and open field). Given that ASD preferentially afflicts male children, these gender-specific behavioral abnormalities in mice are especially interesting.

Methods

Research subjects: Plasma from mothers with an ASD child was obtained from the Simons Simplex Collection (SSC, sfari.org/resources/simons-simplex-collection) (35). Control plasma from women of childbearing age were obtained from the North Shore-LIJ Health System clinical laboratory and participants in a registry at the Feinstein Institute for Medical Research worldwideweb.gapregistry-.org). Both cohorts were described previously (36). All individuals provided informed consent through the appropriate institutional review boards.

Sample Collection: Blood was collected into heparinized tubes from consenting mothers enrolled in the SSC, previously identified as having brain-reactive antibodies (36). The protocol was approved by the SSC as well as by the Feinstein Institute for Medical Research Institute Review Board.

Single cell sorting: Isolation of single human memory brain-reactive B cells was performed as previously described (37) with several modifications. B cells were purified from fresh mononuclear cells by negative selection using a B cell kit (StemCell Technology). They were then incubated for 30 min at room temperature (RT) with human fetal brain lysate (3 mg per ml, Nouvus) labeled with biotin using the EZ-Link Sulfo-NHS-Biotin labeling kit (Life Technologies). Cells bound by biotinylated brain antigens were isolated with a biotin selection kit (StemCell Technologies) and stained with FITC conjugated anti-human CD19, phycoerythrin (PE) conjugated anti-human CD27 and allophycocyanin (APC) streptavidin to allow the separation of $CD19^+$, $CD27^+$, brain lysate memory B cells. As a control, the fraction that initially was identified as non brain-reactive was incubated with biotinylated brain antigen and stained as described above. No APC positive cells were detected in this fraction. Finally, $CD19^+$, $CD27^+$, $APC^+$ single cells were isolated on a BD FACSAria as described in (38).

cDNA Synthesis and RT-PCR: cDNA synthesis of individual IgH (γ only) and IgL chain (k or l) was performed as previously described (37, 38). Heavy and light chain variable region genes were ligated into IgG1 or k constant region containing plasmids (a gift from M. Nussenzweig, Rockefeller University, NY).

Antibody Production: Antibodies were expressed in vitro as described previously (38), with few modifications. In brief, 24 h before transfection with both heavy and light chain plasmids, human embryonic kidney fibroblast 293T (HEK-293T) cells were split into a 100×20 mm culture dish in high glucose DMEM (HyClone, GE Healthcare), supplemented with heat inactivated fetal bovine serum (FBS, 10%), glutamine (1%) and penicillin-streptomycin (1%, HyClone, GE Healthcare). Subsequently, 8 h before transfection, the medium was changed to SFM4Transfx-293 (HyClone, GE Healthcare) supplemented with glutamine (1%) and penicillin-streptomycin (1%). Cells were then cotransfected with plasmid DNA encoding IgH and IgL chains (5 μg), using Lipofectamine 2000 (Life Technologies). Supernatants were collected after 7 days of culture. Antibodies were purified on protein G-sepharose (GE Healthcare, Life Technologies), eluted with glycine buffer (0.1 M, pH 3.5) and neutralized in Tris-HCl (1 M, pH 8). Antibody concentrations in supernatants were determined by anti-human IgG ELISA (37, 38). Purified antibodies was dialyzed extensively against PBS; their integrity was determined by nonreducing SDS gels stained with Coomassie blue and their concentration was measured by both anti-human IgG ELISA (37, 38) and Nanodrop.

Binding assays using transfected HEK-293T cells: Plasma and the human monoclonal antibodies, C6 and B1, (39) were analyzed for binding to Caspr2 using a live cell-based immunofluorescence assay as previously described (40). HEK-293T cells were transfected using Tgfp-Caspr2 or Tgfp vector (Origene) and cultured for 72 h. Cells were stained with C6 or B1 (10 mg per ml in PBS/10% FBS). Antibody binding to Caspr2 transfected cells was detected by Alexa 594-conjugated goat anti-human IgG (Life Technologies). To test for the presence of anti-Caspr2 antibodies in plasma, cells were blocked with goat IgG (Sigma-Aldrich) in PBS and FCS (10%), incubated with pre-absorbed (rabbit liver powder, Sigma-Aldrich) plasma samples (dilution 1:100 and 1:200). IgG binding was detected with Alexa 594-conjugated goat anti-human IgG (Life Technologies). Dead cells were visualized with DAPI staining (Sigma-Aldrich) and live cells were analyzed for Caspr2-IgG binding. Commercially available Anti-Caspr2 antibody directed to an extracellular epitope (NeroMab! UC Davis, Calif.) served as positive control. Anti-Caspr2 antibody directed to a cytoplasmic epitope (Abcam) served as negative control. Cells transfected with tGFP vector and non-transfected cell also served as controls.

Caspr2 protein expression: Embryonic brains and placentas were harvested and immediately frozen in liquid nitrogen and stored (−80° C.). Brains and placentas were homogenized in ice cold homogenization buffer containing sucrose (0.32 M), HEPES (10 mM), EDTA (2 mM), and protease and phosphatase inhibitors (Fisher Scientific), Homogenized brains were then centrifuged (1000×g) for 15 min. The supernatant was recovered and centrifuged again at 200, 000×g. The pellet was re-suspended in buffer and centrifuged again at 200,000×g. Finally, pellets were resuspend in lysis buffer (20 mM Tris-HCl pH 8, 137 mM NaCl, 10% glycerol, 1% NP-40, 2 mM EDTA) and stored (−80° C.). To determine protein concentration, samples were treated with Compat-Able™ protein assay preparation reagent kit (Thermo scientific) and assayed by BCA protein assay kit (Thermo scientific). Brain and placenta membrane lysates were subjected to SDS-PAGE electrophoresis using NuPAGE (Invitrogen) and transferred to PDVF membranes. Membranes were stained in blocking buffer for 1 h at RT (4% milk, 0.1% PBS-Tween) followed by incubation with anti-Caspr2 monoclonal antibody (Abcam) (1:500 in blocking buffer) overnight at 4° C. Membranes were stained with anti-rabbit IR Dye 680CW and visualized using an Odyssey Infrared Imaging System (LI-COR Biosciences). Sodium potassium ATPase was detected by antibody (Abcam, 1:10, 0000) and used as the loading control. Secondary antibody alone showed no binding.

Caspr2 RNA expression: Total RNA was extracted from brain and placenta with an RNeasy kit (Qiagen) and subjected to reverse transcription with an iScript cDNA synthesis kit (Bio-Rad). cDNA was analyzed by quantitative polymerase chain reaction (qPCR) with a LightCycler 480 master mix with TaqMan probes for mouse CNTNAP2 and Polr2A (Applied Biosystems, Thermo Fisher Scientific). Data were normalized to Polr2a; relative induction was calculated by ΔΔCt.

Antibody administration to pregnant dams: C57BL/6 mice (6-8 weeks old) were obtained from the Jackson Laboratory. Animal use was in accordance with institutional guidelines of the Feinstein Institute for Medical Research. For timed pregnancy, 2 females and 1 male were housed together for 14 h. The time when the male mouse was removed from the cage was designated embryonic (E) day 0.5. At E13.5, either C6 antibody (200 mg) or B1 control antibody (200 mg) were administrated by retro-orbital injection to time-pregnant mice under light anesthesia (5). Embryos were harvested at E15.5 and processed for sex identification (described in (41)) and fetal brain pathology. Additional pregnancies were allowed to reach full term.

Immunohistology of fetal brains: E15.5 brains were fixed in paraformaldehyde (4%) overnight at 4° C. followed by sucrose solution (30%) for 48 h at 4° C. and then frozen in OCT. compound (Sakura) on dry ice and stored (−80° C.). Sagittal sections were cut (12 μm thick) on a Cryostat (Leica) and mounted on gelatin-coated slides and stored (−80° C.). Prior to staining, sections were thawed to RT, rinsed twice with PBS and blocked for 1 h with PBS (5%) with bovine serum albumin (BSA) in Triton X100 (0.1%) at RT. Anti-PH3$^+$ antibody (1:100, Millipore) or anti-nestin antibody (1:200, Millipore) and DAPI (1 μg per ml, Life Technologies) were added overnight at 4° C. After washing in PBS/0.1% Tween, antibody binding was detected using Alexa 488 goat anti-rabbit or anti-mouse IgG (Life Technologies) and visualized with an Axio-Imager (Z-1, Axio-Vision 4.7, Zeiss). PH3$^+$ cell quantification was performed as described in (39). Cortical plate and cortical width measurements were obtained from multiple sections of each animal, described in (39)

Immunohistology of adult brains: Brain sections were prepared by anesthetizing mice with isoflurane prior to perfusion. They were perfused with paraformaldehyde (4%), following replacement of blood with heparinized preperfusion buffer. Immunostaining for brain-reactive antibodies from plasma or cell supernatant was performed as described before (36) on non-manipulated C57BL/6 (Jackson Laboratories) or CNTNAP2−/− mice (a gift from Dr. Brett S. Abrahams, Albert Einstein College of Medicine, NY).

Golgi staining and analysis: Mice exposed in utero to antibody were studied at 2 weeks or 16-20 weeks of age. Preparation of brains and Golgi staining were done by FD Rapid GolgiStain Kit (Ellicott City, Md.), according to the manufacturer's protocol. Coronal sections (100 μm thick) of the CA1 region of the hippocampus were analyzed. To be included in the analysis of spines or dendritic arborization, a neuron had to include apical dendrites and a cell body. The arbor needed to be distinguished visually from nearby neurons. For the spine analysis, Z-stack (0.5-µm separation) photomicrographs of the CA1 pyramidal layer (N.A.=1.4; Axio-Imager. Z-1, Axio-Vision 4.8, Zeiss). Images were transferred to a software program (Neurolucida, MBF) that displayed the Z stack information so that the spines on the dendrites were visualized, identified and counted. For dendrite analysis. Z stack (2.0-µm separation, 345×273-µm tiles, N.A.=0.75) were collected, the files were transferred for analysis, and the tracing of the dendritic arbor was quantified and analyzed.

Parvalbumin staining: For this analysis, we used 16-20 week old mice that had behavioral assessment. Brains were sectioned by microtome (40 µm thick) and every fourth section was collected and mounted as before (8). Every eighth Sections were incubated in anti-parvalbumin antibody (Abcam) at a 1:500 dilution in PBS (0.1 M, pH 7.4) overnight at 4° C., and then washed and incubated with biotinylated anti-rabbit IgG (1:200, Vector Laboratories) and avidin-biotin horseradish peroxidase complex at a 1:100 dilution for 1 h followed by a 1:200 solution from Vectastain Elite ABC Kit (Vector, PK-6100), and 3,3'-diaminobenzidine (DAB, 0.05%) with hydrogen peroxide (0.003%). Sections were dehydrated and coverslipped. For quantification, we counted neurons that were positive for the parvalbumin antibody stain from matched coronal sections across the stratum pyramidale of CA1 region of the dorsal hippocampus (Br-1.20 µm to −1.80 µm). (N.A.=0.45, 600×200-µm tiles; Axio-Imager Z1; Zeiss). Comparable volumes were sampled (on average±sem, C6=0.154±0.005 mm$^2$, B1=0.145±0.003 mm$^2$, P=0.18).

Behavioral assessment: Mice that were exposed in utero to C6 or B1 were assessed at 10-14 weeks of age. They were maintained on a reverse schedule of darkness (09:00 to 21:00) and light (21:00 to 9:00), with ad libitum access to food and water. One week before testing, mice were handled for 5 days in sessions of 5-10 min during the dark period of their circadian cycle. A behavioral screen (43) was conducted to ascertain that autonomic responses and neurological reflexes were normal in C6-exposed mice (data not shown). An open field test was used to examine that locomotion was normal in C6-exposed mice; each mouse was placed in the center of a square arena (40 cm on the side) with black walls (30 cm high) and was allowed to move freely for 10 min. Animal behavior was recorded with a centrally-placed video camera using video tracking software (EthoVision v8.5, Noldus, Attleboro, Mass., USA). We also analyzed the occupancy of the center of the arena (10×10 cm square) as a measure of anxiety and found that C6-exposed mice were comparable to B1-exposed mice (data not shown). The behavioral tests resembling the core symptoms of ASD were the marble burying assay, the social preference test, and the clockmaze task. They were performed sequentially, and a resting period of at least 48 h occurred between tests. The marble burying assay (44) was conducted in a cage (38×26 cm$^2$, 18 cm high walls) with soft bedding (4.5 cm deep), in which 20 black glass marbles (1.2 cm diameter) were placed in a 4×5 arrangement. The day before the experiment each mouse was familiarized to the cage (without the marbles) for 20 min and the next day, it was placed in the cage (with marbles) for 30 min. The number of marbles buried (>50% marble covered by bedding material) was recorded. The social preference test was performed in a Y-shaped maze (each arm was 27×14 cm$^2$, 20 cm high walls made of Plexiglas) with a thin layer of bedding placed on the floor. One arm of the Y maze contained a novel object (made of plastic, ~5 cm diameter and 5 cm in height, located at the end of the arm), a second arm had a mouse (placed inside an inverted strainer cup) that had never been in contact with the test mouse, while the third arm was empty. The use of the strainer cup containing the novel mouse ensured that social approach was initiated by the subject mouse only. A day prior to the test, each mouse was placed in the empty Y maze for 10 min, and the next day it was placed for 10 min and its behavior was recorded (Ethovision v8.5). The object was cleaned with ethanol and water between each run. The times spent exploring the object and the novel mouse were used to analyze social preference. The clockmaze task (43) was performed in a circular maze with 12 exits that were located in the wall of the arena like the numbers on the face of a clock. All exits were blocked (black plugs) except for one that led to a tunnel. Mice learned to escape from the arena, which was filled with water (20° C.) to 2 cm depth, sufficient to wet the underside of the belly of mice and provide motivation to find the exit. In the first phase, each animal underwent 6 trials per day, on 2 consecutive days, with an inter-trial interval of at least 20 min. In the second phase, the location of the exit was changed and mice underwent 6 trials on 1 day. The trials were recorded with software (Ethovision 8.5) and the latencies to escape were used to measure learning. A flexibility ratio was computed by the following equation: $(L2-L1)/(L2+L1)$, in which L1 was the average inverse of the latency for the last 3 trials in the first phase and L2 was the average inverse of the latency for the first 3 trials on the second phase of the task.

Statistical analysis: Analysis of variance (ANOVA) was used as well as Student's t-test for datasets that were normally distributed (and with samples larger than 10). For smaller datasets, the Mann-Whitney test was used. To analyze categorical data, a Chi-squared test for independence was used. The nonparametric Kolmogorov Smirnov test was used for large datasets that were not normally distributed. All tests were performed with the statistical toolbox of Origin (versions 9 and 11), and are indicated in the text. Values were considered significant for $p<0.05$.

REFERENCES

1. *Diagnostic and statistical manual of mental disorders* (5th ed.). A. P. Association, Ed., (American Psychiatric Publishing, Arlington, Va., 2013).
2. H. O. Atladottir et al., *Pediatrics* 124, 687 (August, 2009).
3. N. Risch et al., *Am J Psychiatry*, (Jun. 27, 2014).
4. H. O. Atladottir, T. B. Henriksen, D. E. Schendel, E. T. Parner, *Pediatrics* 130, e1447 (December, 2012).
5. P. H. Patterson, *Brain Behavior Immunity* 26, 393 (2012).
6. V. Mazina et al., *J Dev Behav Pediatr* 36, 61 (February-March, 2015).
7. V. Braniste et al., *Sci Transl Med* 6, 263ra158 (Nov. 19, 2014).
8. B. Diamond, G. Honig, S. Mader, L. Brimberg, B. T. Volpe, *Annu Rev Immunol* 31, 345 (2013).
9. L. Brimberg, A. Sadiq, P. K. Gregersen, B. Diamond, *Mol Psychiatry* 18, 1171 (November, 2013).
10. L. A. Croen et al., *Biological psychiatry* 64, 583 (Oct. 1, 2008).
11. P. Dalton et al., *Annals of neurology* 53, 533 (April, 2003).
12. M. D. Bauman et al., *Transl Psychiatry* 3, e278 (2013).
13. T. Tiller et al., *J Immunol Methods* 329, 112 (Jan. 1, 2008).
14. S. Poliak et al., *Neuron* 24, 1037 (December, 1999).
15. S. Poliak et al., *J Cell Biol* 162, 1149 (Sep. 15, 2003).

16. O. Varea et al., *Proc Natl Acad Sci USA* 112, 6176 (May 12, 2015).
17. O. Penagarikano et al., *Cell* 147, 235 (Sep. 30, 2011).
18. J. Y. Lee et al., *Nature medicine* 15, 91 (January, 2009).
19. J. A. Markham et al., *Neuroscience* 116, 71 (2003).
20. J. R. Casanova, M. Nishimura, J. W. Swann, *Brain Res Bull* 103, 39 (April, 2014).
21. G. R. Anderson et al., *Proc Natl Acad Sci USA* 109, 18120 (Oct. 30, 2012).
22. J. L. Silverman, M. Yang, C. Lord, J. N. Crawley, *Nature reviews. Neuroscience* 11, 490 (July, 2010).
23. L. Wang et al., *The Journal of experimental medicine* 209, 1083 (Jun. 4, 2012).
24. M. Alarcon et al., *Am J Hum Genet* 82, 150 (January, 2008).
25. K. A. Strauss et al., *N Engl J Med* 354, 1370 (Mar. 30, 2006).
26. A. J. Verkerk et al., *Genomics* 82, 1 (July, 2003).
27. G. C. Tan, T. F. Doke, J. Ashbumer, N. W. Wood, R. S. Frackowiak, *Neuroimage* 53, 1030 (Nov. 15, 2010).
28. M. L. Simms, T. L. Kemper, C. M. Timbie, M. L. Bauman, G. J. Blatt, *Acta Neuropathol* 118, 673 (November, 2009).
29. R. M. Deacon, *Nat Protoc* 1, 122 (2006).
30. J. H. Kogan, P. W. Frankland, A. J. Silva, *Hippocampus* 10, 47 (2000).
31. *MMWR Surveill Summ* 63, 1 (Mar. 28, 2014).
32. E. Lancaster et al., *Ann Neurol* 69, 303 (February, 2011).
33. S. R. Irani et al., *Brain* 133, 2734 (September, 2010).
34. Tiller, T, et al. Efficient generation of monoclonal antibodies from single human B cells by single cell RT-PCR and expression vector cloning. *J Immunol Methods* 329, 112-124 (2008).
35. G. D. Fischbach, C. Lord, *Neuron* 68, 192 (Oct. 21, 2010).
36. L. Brimberg, A. Sadiq, P. K. Gregersen, B. Diamond, *Mol Psychiatry* 18, 1171 (November, 2013).
37. J. Zhang et al., *J Immunol Methods* 338, 79 (Sep. 30, 2008).
38. T. Tiller et al., *J Immunol Methods* 329, 112 (Jan. 1, 2008).
39. J. Y. Lee et al., *Nature medicine* 15, 91 (January, 2009).
40. S. Mader et al., *PLoS One* 5, e10455 (2010).
41. L. Wang et al., *The Journal of experimental medicine* 209, 1083 (Jun. 4, 2012).
42. L. A. DeGiorgio et al., *Nat Med* 7, 1189 (November, 2001).
43. S. S. Chavan et al., *Mol Med* 18, 930 (2012).
44. A. Thomas et al., *Psychopharmacology* (Berl) 204, 361 (June, 2009).

What is claimed is:

1. A method of inhibiting or reducing development of an autism spectrum disorder in a fetus or an infant comprising administering to a mother pregnant with the fetus prior to the fetus being born as an infant, an amount of an agent comprising a peptide comprising the sequence of an extracellular portion of potassium voltage-gated channel subfamily A regulatory beta subunit 2 (KCNAB2) effective to inhibit or reduce development of an autism spectrum disorder in the fetus or the infant.

2. The method of claim 1, wherein the KCNAB2 is human.

3. The method of claim 1, wherein the agent comprises a fusion protein which comprises a peptide comprising the sequence of an extracellular portion of a KCNAB2.

4. The method of claim 1, wherein the mother has been diagnosed as at risk for an autism spectrum disorder in her fetus by a method comprising obtaining a sample from the mother's blood and quantifying the level of antibody directed to KCNAB2 in the sample, and comparing the level so quantified to a predefined control level of the respective antibody, wherein an antibody level in the sample in excess of the control level has been determined, so diagnosing the mother as at risk for an autism spectrum disorder in her fetus.

5. The method of claim 1, further comprising an initial step of receiving identification of the mother as being at risk for an autism spectrum disorder in a fetus she is pregnant with and administering the amount of an agent to the mother so identified.

6. The method of claim 1, wherein the method is of inhibiting or reducing development of an autism spectrum disorder in a fetus and wherein the amount of agent is administered to a mother pregnant with the fetus.

7. The method of claim 1, wherein the method is of inhibiting or reducing development of an autism spectrum disorder in an infant comprising administering to a mother pregnant prior to the fetus being born as an infant while the mother is pregnant.

8. The method of claim 1, wherein the fetus or infant is male.

9. A method of inhibiting or reducing development of an autism spectrum disorder in a fetus or an infant comprising extracorporeally contacting blood of a mother (i) pregnant with the fetus or (ii) prior to the fetus being born as an infant while the mother is pregnant, with an amount of an agent comprising a peptide comprising the sequence of an extracellular portion of a potassium voltage-gated channel subfamily A regulatory beta subunit 2 (KCNAB2) so as to reduce the blood levels of an antibody directed to KCNAB2, and recirculating the blood so treated back into the mother effective to inhibit or reduce development of an autism spectrum disorder in the fetus or the infant.

10. The method of claim 9, wherein the fetus or infant is male.

* * * * *